(12) United States Patent
Min et al.

(10) Patent No.: US 10,517,535 B2
(45) Date of Patent: Dec. 31, 2019

(54) METHOD FOR CONTROLLING WEARABLE DEVICE AND WEARABLE DEVICE (71) Applicant: SAMSUNG ELECTRONICS CO., LTD., Suwon-si (KR)

(72) Inventors: Jung-hye Min, Yongin-si (KR); Moon-joo Lee, Suwon-si (KR); In-kuk Yun, Suwon-si (KR); Myung-jin Eom, Seoul (KR); Nam-suk Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 59 days.

(21) Appl. No.: 15/121,856

(22) PCT Filed: Mar. 23, 2015

(86) PCT No.: PCT/KR2015/002805
§ 371 (c)(1),
(2) Date: Aug. 26, 2016

(87) PCT Pub. No.: WO2015/142134
PCT Pub. Date: Sep. 24, 2015

(65) Prior Publication Data
US 2017/0112438 A1 Apr. 27, 2017

(30) Foreign Application Priority Data
Mar. 21, 2014 (KR) .......................... 10-2014-0033647

(51) Int. Cl.
*A61B 5/0402* (2006.01)
*A61B 5/0205* (2006.01)
(Continued)

(52) U.S. Cl.
CPC ........ *A61B 5/6803* (2013.01); *A61B 5/02055* (2013.01); *A61B 5/02438* (2013.01);
(Continued)

(58) Field of Classification Search
CPC . A61B 5/02433; A61B 5/6803; A61B 5/6816; A61B 5/742; A61B 5/0478;
(Continued)

(56) References Cited

U.S. PATENT DOCUMENTS 7,211,053 B2    5/2007  Marmaropoulos et al.
D606,656 S     12/2009  Kobayashi et al.
(Continued)

FOREIGN PATENT DOCUMENTS

CN   1578639 A    2/2005
CN   2798135 Y    7/2006
(Continued)

OTHER PUBLICATIONS

International Search Report and Written Opinion dated Jun. 29, 2015 issued by the International Searching Authority in counterpart International Application No. PCT/KR2015/002805 (PCT/ISA/210/220/237).
(Continued)

*Primary Examiner* — Carl H Layno
*Assistant Examiner* — Jon Eric Morales
(74) *Attorney, Agent, or Firm* — Sughrue Mion, PLLC (57) ABSTRACT Provided are a method of controlling a wearable device and a wearable device. The method of controlling the wearable device includes: determining whether a sensor provided in the wearable device is in an activated state; controlling an adherency controller for adjusting adherency between the sensor and a body of a user wearing the wearable device based on whether the sensor is in the activated state; and detecting a biosignal via the sensor.

7 Claims, 8 Drawing Sheets (51) Int. Cl.
*A61B 5/00* (2006.01)
*A61B 5/0488* (2006.01)
*A61B 5/024* (2006.01)
*A61B 5/01* (2006.01)
*A61B 5/021* (2006.01)
*A61B 5/053* (2006.01)
*A61B 5/08* (2006.01)
*A61B 5/113* (2006.01)

(52) U.S. Cl.
CPC .......... *A61B 5/0402* (2013.01); *A61B 5/0488* (2013.01); *A61B 5/6831* (2013.01); *A61B 5/6843* (2013.01); *A61B 5/6885* (2013.01); *A61B 5/01* (2013.01); *A61B 5/021* (2013.01); *A61B 5/0531* (2013.01); *A61B 5/08* (2013.01); *A61B 5/0816* (2013.01); *A61B 5/113* (2013.01); *A61B 2560/029* (2013.01)

(58) Field of Classification Search
CPC ......... A61B 5/0476; A61B 5/16; A61B 5/165; A61B 5/6814; A61B 5/1455; A61B 2562/0219; A61B 5/168; A61B 5/053
USPC .............................................. 600/544; 351/41
See application file for complete search history.

(56) References Cited

U.S. PATENT DOCUMENTS 10,060,790 B2    8/2018   Howell et al.
2007/0109491 A1* 5/2007   Howell .................. G02C 11/10
                                                351/41
2009/0253996 A1* 10/2009  Lee ...................... A61B 5/0476
                                                600/544
2010/0298727 A1   11/2010  Uenishi et al.
2014/0198293 A1*  7/2014   Sweis .................... A61H 5/005
                                                351/158
2016/0317060 A1* 11/2016  Connor ................ A61B 5/4866

FOREIGN PATENT DOCUMENTS

| | | |
|---|---|---|
| CN | 101046557 A | 10/2007 |
| CN | 101848669 A | 9/2010 |
| EP | 1 455 640 B1 | 1/2008 |
| JP | 2002-102179 A | 4/2002 |
| JP | 2005-506467 A | 3/2005 |
| JP | 2014-18234 A | 2/2014 |
| KR | 10-2009-0099147 A | 9/2009 |
| WO | 2009/033181 A1 | 3/2009 |

OTHER PUBLICATIONS

Communication dated Jul. 2, 2018, issued by The State Intellectual Property Office of P.R. China in counterpart Chinese Application No. 201580015376.2.

Communication dated Oct. 18, 2019, issued by the Korean Intellectual Property Office in counterpart Korean Application No. 10-2014-0033647.

* cited by examiner

METHOD FOR CONTROLLING WEARABLE DEVICE AND WEARABLE DEVICE

TECHNICAL FIELD

The present invention relates to a method of controlling a wearable device and a wearable device, and more particularly, to a method of controlling adherency between a sensor provided in the wearable device for detecting a biosignal and a body of user wearing the wearable device, and an apparatus for controlling the adherency.

BACKGROUND ART

Electronic devices have become smaller and lighter according to the development of technology and can have a variety of configurations. Accordingly, wearable devices that can be worn by a user have been developed. For example, smart watches or smart glasses have been developed. A smart watch refers to an embedded system wristwatch that generally has more advanced features than a typical watch. A smart glass refers to a wearable computer that is generally equipped with a head mounted display (HMD). The wearable devices can be classified into a standalone device and an interlocking device. A standalone device is equipped with a self input/output device, an arithmetic unit, a storage device, and a communication device, and can be used alone. An interlocking device refers to a device that can be used after being connected with a separate device such as a smart phone.

Since the wearable device is worn on a user, it is advantageous for obtaining a biosignal from the user. Thus, a wearable device including various sensors has been developed. For example, a smart watch may be provided with a glucose sensor or a blood pressure sensor. The wearable device can be equipped with various sensors, such as a biosensor, a motion sensor, a chemical sensor, a temperature sensor, and a position sensor. A biosensor refers to a device for measuring a state or concentration of an organic compound by using a function of a living organism. A motion sensor refers to a device for detecting a movement of the device. For example, the motion sensor can include a gyroscope or an acceleration sensor. A chemical sensor refers to a sensor targeting a chemical material for measurement. A temperature sensor refers to a device for measure a temperature. A position sensor refers to a device for measuring a position such as a ground positioning system (GPS).

However, sensors may have different accuracy according to adherency information provided by the user. Thus, sensors need to be in close contact with the body of the user's body. On the other hand, if a sensor is positioned too close to the user, the user may suffer from pressure and feel uncomfortable.

DETAILED DESCRIPTION OF THE INVENTION

Technical Problem

According to an exemplary embodiment, there are provided a wearable device with a sensor configured to obtain more accurate measurement and a method of controlling the wearable device.

According to another exemplary embodiment, there are provided a wearable device that can be worn more comfortably by a user and a method of controlling the wearable device.

Technical Solution

As a technical means for achieving the above-described technical problems, a method of controlling a wearable device according to an exemplary embodiment includes steps of: determining whether a sensor provided in the wearable device is in an activated state; controlling an adherency controller for adjusting adherency between the sensor and a body of a user wearing the wearable device based on whether the sensor is in the activated state; and detecting a biosignal via the sensor.

Advantageous Effects of the Invention

According to an exemplary embodiment, when adjusting adherency as necessary between a sensor and a body of a user wearing a wearable device, a wearable device can be worn more comfortably by a user.

According to another exemplary embodiment, a sensor can obtain a more accurate measurement.

BEST MODE

As a technical means for achieving the above-described technical problems, a method of controlling a wearable device according to an exemplary embodiment may include steps of: determining whether a sensor provided in the wearable device is in an activated state; controlling an adherency controller for adjusting adherency between the sensor and a body of a user wearing the wearable device based on whether the sensor is in the activated state; and; and detecting a biosignal via the sensor.

In addition, in an exemplary embodiment, the determination of whether the sensor is in the activated state may include a step of checking an operation schedule of the sensor.

In addition, the wearable device according to another exemplary embodiment may further include a band which is wearable on the body of the user, and the controlling of the adherency controller may further include a step of controlling the adherency controller to lengthen or shorten the band.

In addition, the wearable device according to another exemplary embodiment may further include a frame and temples of a pair of glasses, and accordingly, the adherency controller may include a hinge for connecting the frame to each of the temples. The controlling of the adherency controller may include a step of increasing or decreasing an angle of the hinge.

In addition, according to another exemplary embodiment, the detecting of the biosignal may include a step of detecting at least one of action potential of muscles, blood volume, electrical activity of the heart, respiration, heart rate, temperature, and blood pressure.

In addition, as a technical means for achieving the above-described technical problems, the wearable device according to an exemplary embodiment may include: a sensor configured to detect a biosignal from a body of a user wearing the wearable device; an adherency controller configured to adjust adherency between the sensor and the body of the user; and a controller configured to control the adherency controller based on whether the sensor is in an activated state.

In addition, according to another exemplary embodiment, the controller may be configured to determine whether the sensor is in the activated state by checking an operation schedule of the sensor.

In addition, according to another exemplary embodiment, the wearable device may further include a band which is wearable on the body of the user, and the adherency controller is configured to lengthen or shorten the band according to an operation of the controller.

In addition, according to another exemplary embodiment, the wearable device may include a frame and temples of a pair of glasses, the adherency controller may include a hinge for connecting the frame to each of the temples, and the wearable device may be configured to increase or decrease an angle of the hinge.

In addition, according to another exemplary embodiment, the sensor may be configured to detect at least one of EMG, blood volume, ECG, respiration, heart rate, temperature, and blood pressure.

In addition, a computer-readable recording medium having a program recorded thereon, which, when executed by a computer, performs the above-described method.

Mode of the Invention

Reference will now be made in detail to exemplary embodiments, examples of which are illustrated in the accompanying drawings, wherein like reference numerals refer to like elements throughout. The inventive concept may, however, be embodied in many different forms and should not be construed as being limited to the embodiments set forth herein. In the accompanying drawings, a portion irrelevant to a description of the inventive concept will be omitted for clarity. Moreover, like reference numerals refer to like elements throughout.

Throughout the specification, when a portion "is connected with/to" another portion, the present invention should be construed to include not only a case where a portion "is directly connected with/to" another portion, but also a case where a portion "is electrically connected with/to" another portion and a separate device is interposed between these two portions'. In addition, when a portion "includes" an element, another element may be further included, rather than excluding the existence of the other element, unless otherwise described.

Hereinafter, the present invention will be described in detail with reference to the attached drawings.

Figure 1:
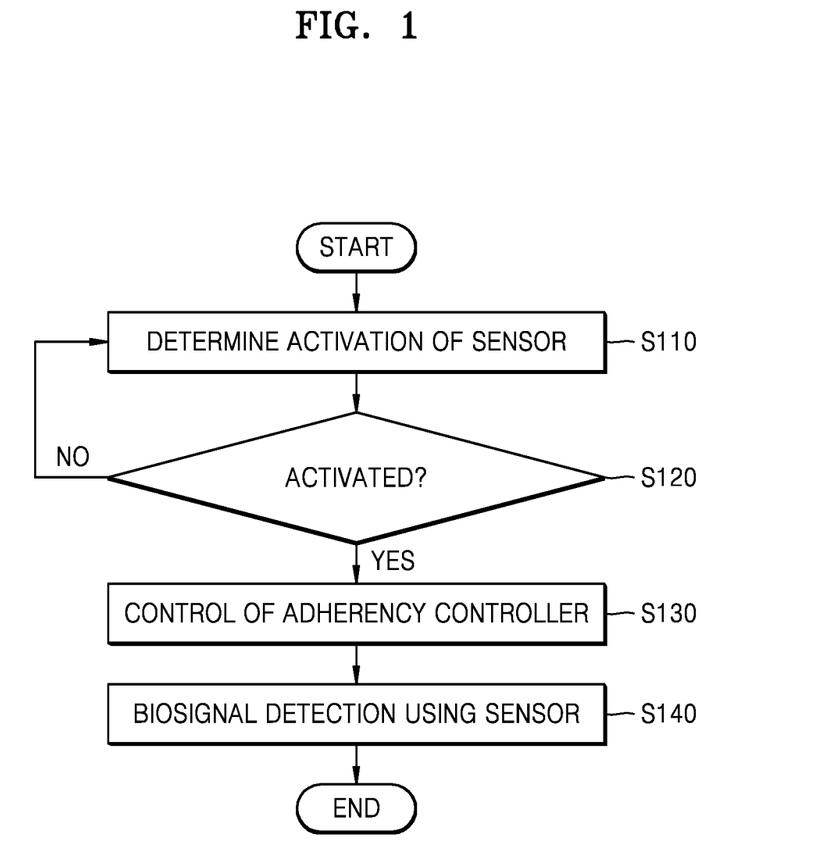
FIG. 1 is a flowchart illustrating a process of controlling a wearable device according to an exemplary embodiment.

FIG. 1 is a flowchart illustrating a process of controlling a wearable device according to an exemplary embodiment. The wearable device according to an exemplary embodiment may include a sensor. For example, the wearable device may include at least one of an electromyography (EMG) sensor, an electrodermal activity sensor, a skin thermometer, a blood volume pulse (BVP) measuring device, an electrocardiogram (ECG) sensor, a respiration sensor, a blood pressure measuring device, and a hear rate measuring device. The EMG sensor means a sensor for detecting an action potential of muscles. The electrodermal activity sensor means a sensor for measuring the conductivity of the skin. The skin thermometer may include a sensor for sensing the temperature of the skin surface. The BVP measuring device means a device for measuring a volume of blood flowing in a blood vessel. The ECG sensor is a sensor for detecting a heart rate-related electric potential on a surface of the body. The respiration sensor is a sensor for measuring quantity and frequency of breathing. The heart rate measuring device indicates the number of the heartbeats during unit time.

First, the wearable device may determine whether the sensor is in an activated state (operation S110). Here, the state of the sensor may be determined in various ways. According to an exemplary embodiment, in the presence of a measured value that is received by the sensor, it is determined that the sensor included in the wearable device is activated. According to another exemplary embodiment, the sensor can be determined whether it is in an activated stated depending on operation schedules of the sensor. For example, when the wearable device includes a body temperature measuring sensor that is scheduled to measure a body temperature once every hour for a minute, the wearable device can determine that the sensor is being activated once every hour for a minute.

When the sensor is determined to be activated (in operation S120) in operation S110, the wearable device can accordingly control the adherency controller. By controlling the adherency controller, the wearable device can adjust adherency between the sensor and the body (operation S130). The adherency controller can be implemented in various ways according to an exemplary embodiment.

According to an exemplary embodiment, the wearable device may include a band which is wearable on the body of the user. The adherency controller may control the band to lengthen or shorten the band included in the wearable device. For example, the band included in the wearable device may include a shape-memory alloy. In this case, the adherency controller can adjust a length of the band by contraction and expansion of the shape-memory alloy.

Figure 5:
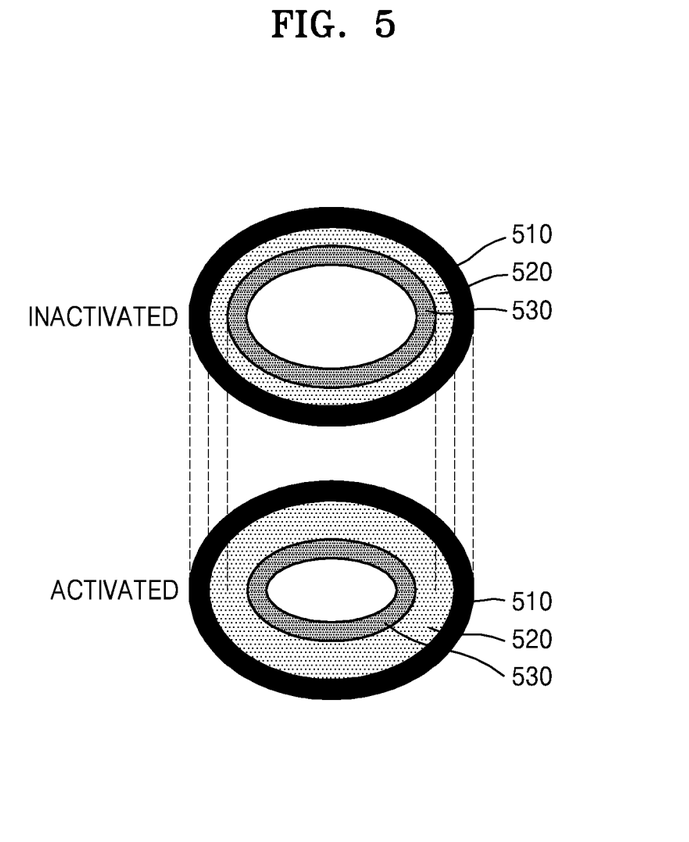
FIG. 5 is a diagram conceptually illustrating a structure of an adherency controller according to an exemplary embodiment.

Alternatively, referring to FIG. 5, FIG. 5 is a diagram conceptually illustrating a structure of the adherency controller according to an exemplary embodiment. The adherency controller according to an exemplary embodiment as shown in FIG. 5 may include an outer band having a fixed length, a sensor 530 positioned on an inner side of the outer band, and an air injector 520 positioned between the outer band and the sensor 530. In operation S130, the adherency controller may inject air into the air injector 520. Accordingly, when the sensor 530 is activated, the adherency controller may adhere the sensor 530 to the body inside the outer band.

Figure 6:
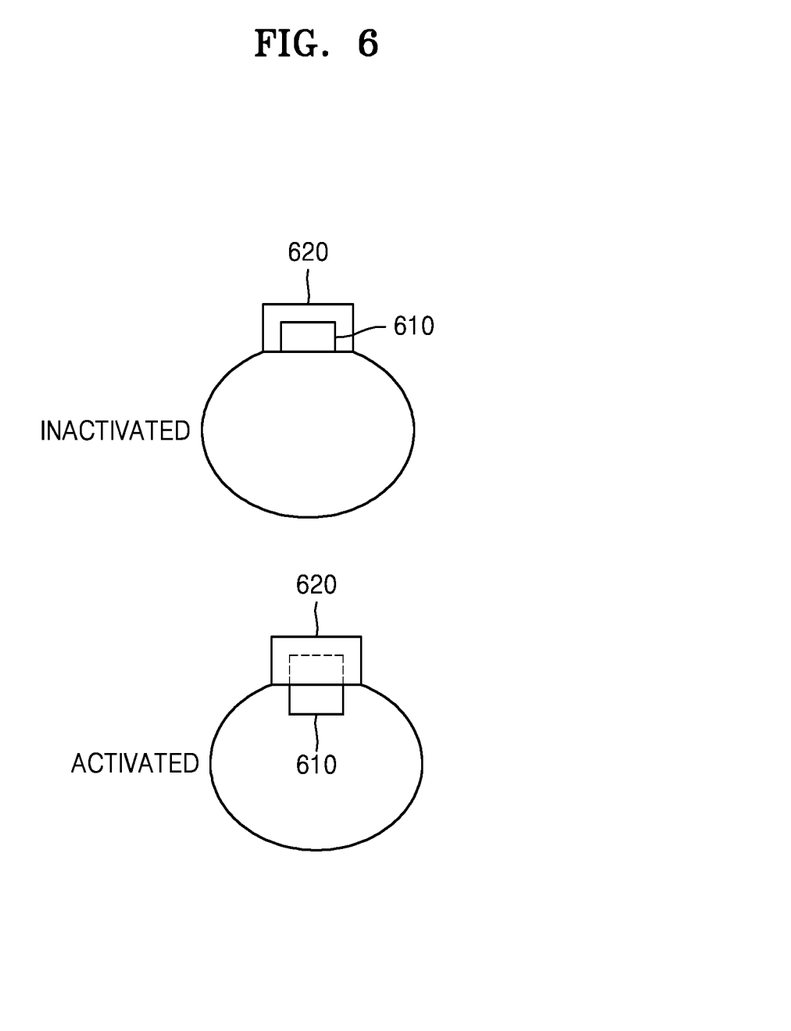
FIG. 6 is a diagram conceptually illustrating a structure of an adherency controller according to another exemplary embodiment.

Alternatively, referring to FIG. 6, FIG. 6 is a diagram conceptually illustrating a structure of the adherency controller according to another exemplary embodiment. The adherency controller according to an exemplary embodiment as shown in FIG. 6 may include a sensor receptor 620 receiving therein a sensor 610 that is in an inactivated state. When the sensor 610 is determined to be activated in operation S120 of FIG. 1, the wearable device may accordingly control the adherency controller to thereby protrude the sensor 610 to the outside of the sensor receptor 620.

In addition, according to another exemplary embodiment, the wearable device may be smart glasses. In this case, the wearable device may include a frame constituting a body of the glasses and temples for supporting the glasses. Here, the adherency controller may include a hinge for connecting the frame for the glasses to each of the temples. Here, the hinge may control an angle between the frame and each of the temples. To control adherency in operation S130, the adherency controller may increase or decrease an angle between the frame and each of the temples.

In addition, according to an exemplary embodiment, the wearable device store a first state of the adherency controller and a second state of the adherency controller, wherein the first state refers to a state of which the sensor is inactivated and the second state refers to a state of which the sensor is activated. Afterwards, when the sensor is determined to be inactivated in operation S120, the wearable device may have the adherency controller in the first state. In addition, when the sensor is determined to be activated in operation S120, the wearable device may have the adherency controller in the second state. Such the first and second states may be considered as factors that determine adherency between the sensor and the wearer's body. For example, the first and second states may each correspond to a different length of the band. The first state or the second state may be set by a user. As the user differently sets the first state or the second state, the wearable device may control the adherency controller to be in appropriate contact with the body of the user wearing the wearable device.

When the adherency between the sensor and the body of the user wearing the wearable device is adjusted in operation S130, the wearable device may detect a biosignal through the sensor adhered to the body of the user wearing the wearable device (operation S140). The wearable device may obtain information according to types of the sensor.

Figure 2:
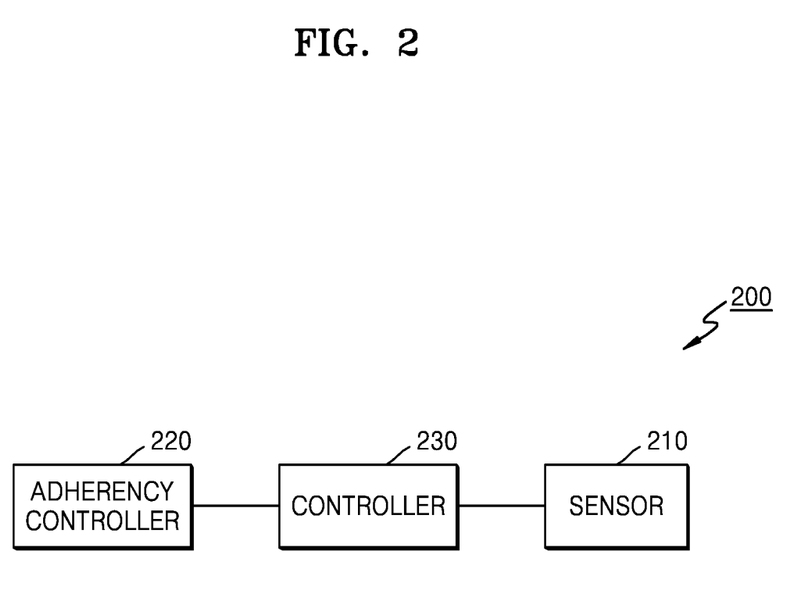
FIG. 2 is a block diagram illustrating a structure of a wearable device according an exemplary embodiment.

FIG. 2 is a block diagram illustrating a structure of a wearable device 200 according to an exemplary embodiment. FIG. 2 is provided to represent one exemplary embodiment of the present invention, and the wearable device 200 according to an exemplary embodiment may include more components than those shown in FIG. 2. In addition, the components shown in FIG. 2 may be replaced with similar components.

The wearable device 200 according to an exemplary embodiment may include a sensor 210, an adherency controller 220, and a controller 230.

The sensor 210 may detect a biosignal from a body of a wearer wearing the wearable device 200. For example, the wearable device 200 may include at least one of an EMG sensor, an electrodermal activity sensor, a skin thermometer, a blood volume pulse (BVP) measuring device, an electrocardiogram (ECG) sensor, a respiration sensor, a blood pressure measuring device, and a hear rate measuring device. The EMG sensor means a sensor for detecting an action potential of muscles. The electrodermal activity sensor means a sensor for measuring the conductivity of the skin. The skin thermometer may include a sensor for sensing the temperature of the skin surface. The BVP measuring device means a device for measuring a volume of blood flowing in a blood vessel. The ECG sensor is a sensor for detecting a heart rate-related electric potential on a surface of the body. The respiration sensor is a sensor for measuring quantity and frequency of breathing. The heart rate measuring device indicates the number of the heartbeats during unit time.

The adherency controller 220 may adjust adherency between the sensor and the wearer's body according to the control of the controller 230. According to an exemplary embodiment, the wearable device may include a band which is wearable on the body of the user. The adherency controller 220 may lengthen or shorten the band included in the wearable device 200. For example, the band included in the wearable device 200 may include a shape-memory alloy. In this case, the adherency controller 220 can adjust a length of the band by contraction and expansion of the shape-memory alloy.

Alternatively, referring to FIG. 5, FIG. 5 is a diagram conceptually illustrating a structure of the adherency controller 220 according to an exemplary embodiment. The adherency controller 220 according to an exemplary embodiment as shown in FIG. 5 may include the outer band having a fixed length, the sensor 530 positioned on an inner side of the outer band, and the air injector 520 positioned between the outer band and the sensor 530. According to the control of the controller 230, the adherency controller 220 may inject air into the air injector 520. Accordingly, when the sensor 530 is activated, the adherency controller 220 may adhere the sensor 530 to the body inside the outer band.

Alternatively, referring to FIG. 6, FIG. 6 is a diagram conceptually illustrating a structure of the adherency controller 220 according to another exemplary embodiment. The adherency controller 220 according to an exemplary embodiment as shown in FIG. 6 may include the sensor receptor 620 receiving therein the sensor 610 that is in an inactivated state. When the sensor 610 is determined to be activated in operation S120 of FIG. 1, the adherency controller 220 may be controlled according to the control of the controller 230 to thereby protrude the sensor 610 to the outside of the sensor receptor 620.

In addition, according to another exemplary embodiment, the wearable device 200 may be smart glasses. In this case, the wearable device 200 may include a frame constituting the body of the glasses and temples for supporting the glasses. Here, the adherency controller 220 may include a hinge for connecting the frame a pair of the glasses to each of the temples. Here, the hinge may control an angle between the frame and each of the temples. To control adherency, the adherency controller 220 may increase or decrease an angle between the frame and each of the temples.

The controller 230 may control each components of the wearable device 200. The controller 230 may control the adherency controller 220 depending on whether the sensor 210 is activated. According to an exemplary embodiment, the controller 230 determines a first state of the adherency controller 220 and a second state of the adherency controller 220, wherein the first state refers to a state of which the sensor 210 is inactivated and the second state refers to a state of which the sensor 210 is activated. The controller 230 may store a memory (not shown). Afterwards, when the sensor 210 is determined to be inactivated, the controller 230 may control the adherency controller 220 to be in the first state. In addition, when the sensor 210 is determined to be activated, the controller 230 may control the adherency controller 220 to be in the second state. Such the first and second states may be considered as factors that determine adherency between the sensor and the body of the user wearing the wearable device. For example, the first and second states may each correspond to a different length of the band. The first state or the second state may be set by a user. As the user differently sets the first state or the second state, the wearable device may control the adherency controller to be in appropriate contact with the body of the user wearing the wearable device.

Figure 3:
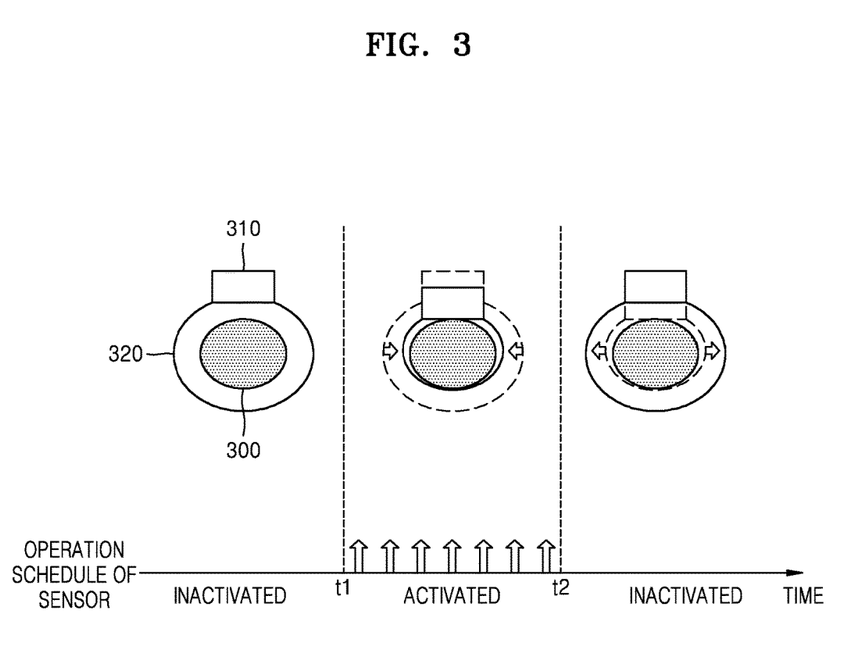
FIG. 3 is a diagram conceptually illustrating an operation of a wearable device according to an exemplary embodiment.

FIG. 3 is a diagram conceptually illustrating an operation of the wearable device including a band 320 according to an exemplary embodiment. FIG. 3 shows an operation of the wearable device in a case where a sensor 310 operates according to a predetermined schedule. The wearable device according to an exemplary embodiment may include the sensor 310 and the band 320. The wearable device may be worn by a user's body 300 by using the band 320. When the sensor 310 is in an inactivated state, the wearable device may control the adherency controller such that the band 320 is lengthened in the first state.

When the sensor 310 is scheduled to be activated at the point of t1, the wearable device may control the adherency controller such that the band 320 is shortened in the second state at the point of t1. As the band 320 is shortened, the sensor 310 may be adhered and fixed on the body 300 of the user wearing the wearable device 200. Next, when the sensor 310 is scheduled to be inactivated at the point of t2, the wearable device may control the adherency controller such that the band 320 may have a same length as in the first state at the point of t2.

Figure 4:
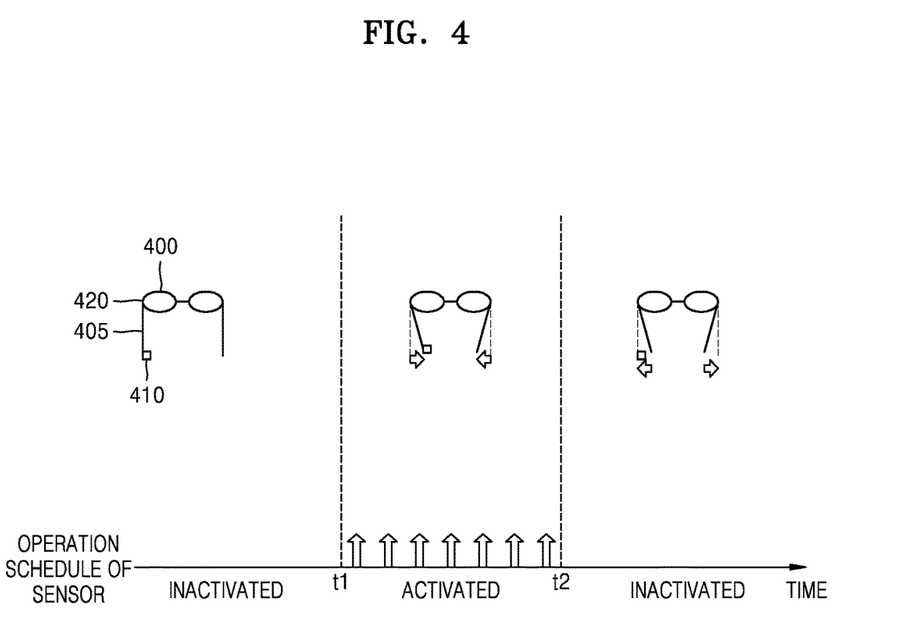
FIG. 4 is a diagram conceptually illustrating an operation of a wearable device according to another exemplary embodiment.

FIG. 4 is a diagram conceptually illustrating an operation of the wearable device including a frame 400 and temples 405 of a pair of glasses according to another exemplary embodiment. FIG. 4 shows an operation of the wearable device in a case where a sensor 410 operates according to a predetermined schedule. The wearable device may include the frame 400 and temples 405 of a pair of glasses, and a hinge 420 connecting the frame 400 to each of the temples 405 and the hinge 420 may be included in the adherency controller. In this regard, the adherency controller may adjust an angle between the frame 400 and each of the temples 405 by using the hinge 420 upon a pressure applied to the frame 400. When the sensor 410 is in an inactivated state, the wearable device may control the adherency controller such that the angle between the frame 400 and each of the temples 405 is large in the first state.

When the sensor 410 is scheduled to be activated at the point of t1, the wearable device may control the adherency controller such that the angle between the frame 400 and each of the temples 405 is small in the second state at the point of t1. Next, when the sensor 410 is scheduled to be inactivated at the point of t2, the wearable device may control the adherency controller such that the wearable device may have a same angle between the frame 400 and each of the temples 405 as the angle in the second state at the point of t2.

Figure 7:
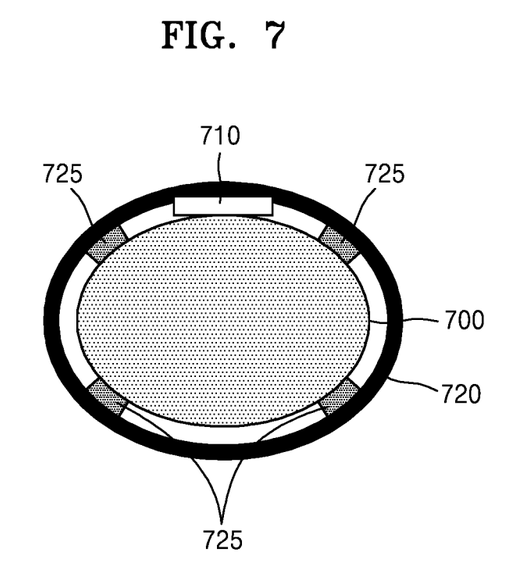
FIG. 7 is a diagram conceptually illustrating a structure of a wearable structure according to an exemplary embodiment.

FIG. 7 is a diagram conceptually illustrating a structure of the wearable structure according to an exemplary embodiment.

According to types of the sensor, when a configuration other than the sensor is in contact with a body of a user wearing the wearable device, the accuracy of the sensor may be degraded. For example, when a configuration other than the sensor is in contact with the skin while measuring the skin temperature, the skin temperature is changed, thereby having difficulties in measuring the exact temperature.

To solve such difficulties, the wearable device according to an exemplary embodiment may include a support 725. When the wearable device includes a band 720 as shown in FIG. 7, the support 725 may be arranged on at least one position of the band 720. According to the position of the support 725, a sensor 710 is in contact with a wearer's body 700, whereas the band 720 is not in contact with the wearer's body 700.

Figure 8:
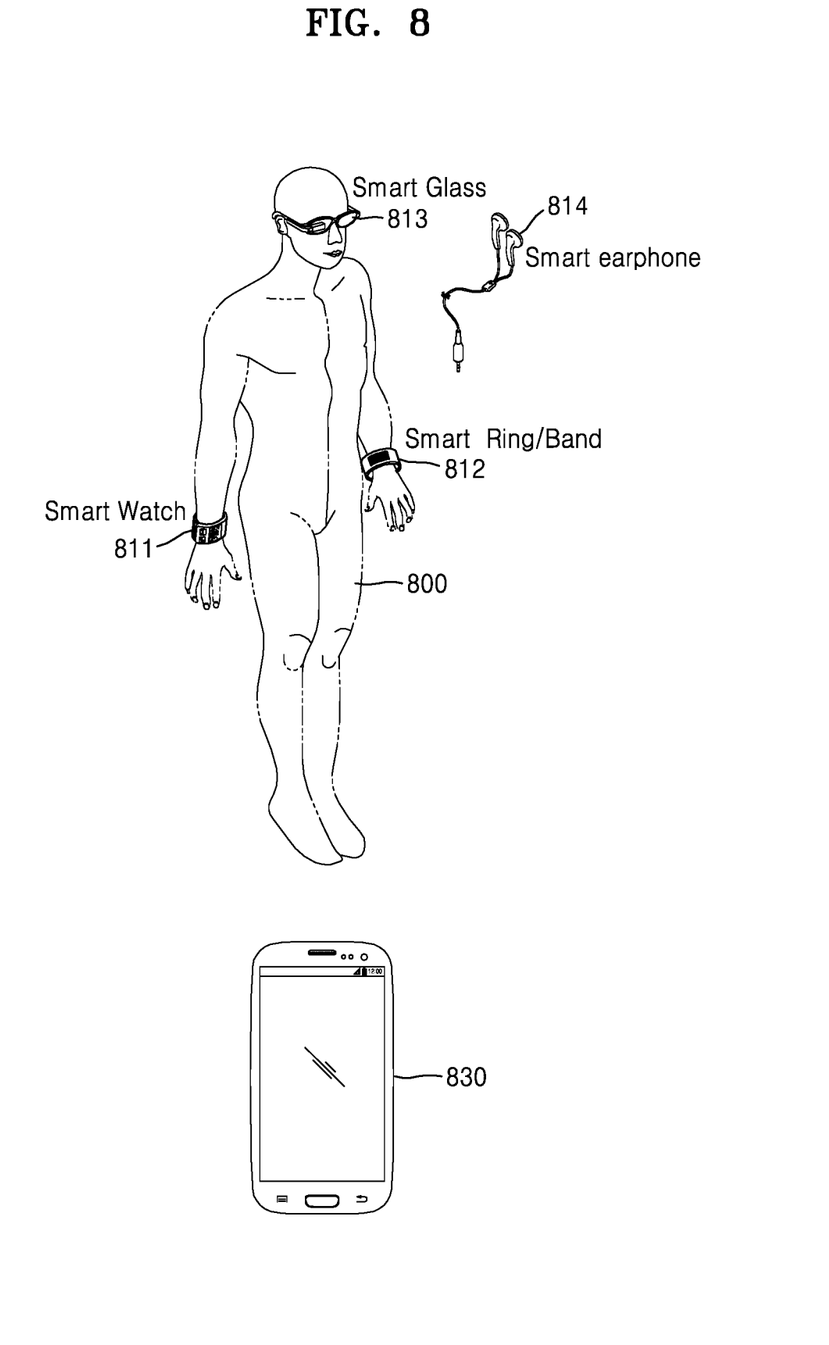
FIG. 8 is a diagram conceptually illustrating an operation of a multi-device.

FIG. 8 is a diagram conceptually illustrating an operation of a multi-device.

*When a user 800 wears a plurality of wearable devices, such as a smart watch 811, a smart ring/band 812, smart glasses 813, and a smart earphone 814, that are capable of measuring a biosignal, a device 830 may register the plurality of wearable devices. The device 830 may include a mobile terminal, a PC, a notebook PC, a tablet PC, or the like, but is not limited thereto. The device 830 may determine the rankings of the wearable devices that can be used for measuring bio-information. For example, the smart earphone 814 may be ranked first by the device 830 in terms of measuring the heart rate. In addition, the smart watch 811 may be ranked second by the device 830. In addition, the smart ring/band 812 may be ranked third by the device 830 in terms of measuring the heart rate. In addition, the smart glasses 813 may be ranked fourth by the device 830 in terms of measuring the heart rate.

Afterwards, the device 830 may determine which wearable device(s) is being worn by a user 800 at a predetermined time to measure the heart rate. When the user 800 wears the smart watch 811, the smart ring/band 812, and the smart glasses 813, the device 830 allows the smart watch 811 to measure the heart rate, the smart watch 811 being ranked highest among the wearable devices worn by the user 800 in terms of measuring the heart rate.

An exemplary embodiment can also be embodied as a storage medium including instruction codes executable by a computer such as a program module executed by the computer. A computer-readable recording medium can be any usable medium which can be accessed by the computer and includes all volatile/non-volatile and removable/non-removable media (e.g., RAM and ROM). Further, the computer-readable recording medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes any information transmission medium. For example, the computer storage medium may be implemented as a read-only memory (ROM), a random access memory (RAM), a flash memory, a CD, a DVD, a magnetic disk, or a magnetic tape.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A method of controlling a wearable device, the method comprising:
   storing, in a memory of the wearable device, information regarding a first state and a second state of an adherency controller included in the wearable device, wherein the first state is a state in which a sensor provided in the wearable device does not detect a biosignal from a body of a user wearing the wearable device and the second state is a state in which the sensor detects the biosignal from the body of the user;

determining, by a controller of the wearable device, whether the sensor detects the biosignal; and controlling, by the controller, the adherency controller to be in the first state or the second state based on whether the sensor detects the biosignal, wherein the adherency controller comprises a band wearable on the body of the user, and wherein the controlling comprises:
controlling to lengthen the band in response to determining that the sensor does not detect the biosignal; and
shortening the band in response to determining that the sensor detects the biosignal.

2. The method of claim 1, wherein the sensor is activated according to an operation schedule of the sensor.

3. The method of claim 1, further comprising:
detecting, by the controller via the sensor, at least one of an action potential of muscles of the user, a blood volume of the user, electrical activity of a heart of the user, a respiration of the user, a heart rate of the user, a temperature of the user, and a blood pressure of the user.

4. A non-transitory computer-readable recording medium having a program recorded thereon, which, when executed by a computer, performs the method of claim 1.

5. A wearable device comprising:
a sensor configured to detect a biosignal from a body of a user wearing the wearable device;
an adherency controller configured to adjust adherency between the wearable device and the body of the user;
a memory storing information regarding a first state and a second state of the adherency controller, wherein the first state is a state in which the sensor does not detect the biosignal and the second state is a state in which the sensor detects the biosignal; and
a controller configured to store, in the memory, the information regarding the first state and the second state, determine whether the sensor detects the biosignal, and control the adherency controller to be in the first state or the second state based on whether the sensor detects the biosignal,
wherein the adherency controller further comprises a band wearable on the body of the user, and
wherein the controller is configured to control the adherency controller to lengthen the band in response to the sensor not detecting the biosignal and shorten the band in response to determining the sensor detecting the biosignal.

6. The wearable device of claim 5, wherein the controller is configured to determine whether the sensor is activated according to an operation schedule of the sensor.

7. The wearable device of claim 5, wherein the sensor detects at least one of an action potential of muscles of the user, a blood volume of the user, electrical activity of a heart of the user, a respiration of the user, a heart rate of the user, a temperature of the user, and a blood pressure of the user.

* * * * *